US012721951B2

(12) United States Patent
Chen et al.

(10) Patent No.: US 12,721,951 B2
(45) Date of Patent: Sep. 1, 2026

(54) SAFE PUNCTURE NEEDLE

(71) Applicant: Zhejiang Kindly Medical Devices Co., Ltd., Wenzhou (CN)

(72) Inventors: Xu Chen, Wenzhou (CN); Qian Zhang, Wenzhou (CN); Hong Chen, Wenzhou (CN); Yuanxian Zheng, Wenzhou (CN); Zhongshichao Chi, Wenzhou (CN); Zhuoyuan Lou, Wenzhou (CN)

(73) Assignee: Zhejiang Kindly Medical Devices Co., Ltd., Wenzhou (CN)

( * ) Notice: Subject to any disclaimer, the term of this patent is extended or adjusted under 35 U.S.C. 154(b) by 526 days.

(21) Appl. No.: 18/223,276

(22) Filed: Jul. 18, 2023

(65) Prior Publication Data

US 2024/0075217 A1 Mar. 7, 2024

(30) Foreign Application Priority Data

Sep. 7, 2022 (CN) ......................... 202222394755.7

(51) Int. Cl.
*A61M 5/32* (2006.01)
*A61M 5/158* (2006.01)
*A61M 5/162* (2006.01)
*A61M 25/06* (2006.01)

(52) U.S. Cl.
CPC ........ *A61M 5/321* (2013.01); *A61M 25/0618* (2013.01); *A61M 2005/1581* (2013.01); *A61M 5/1626* (2013.01); *A61M 2005/325* (2013.01)

(58) Field of Classification Search
CPC .............. A61M 5/321; A61M 25/0618; A61M 5/1626; A61M 5/3243; A61M 2005/1581; A61M 2005/3247; A61M 2005/325
See application file for complete search history.

(56) References Cited

U.S. PATENT DOCUMENTS

| | | | | |
|---|---|---|---|---|
| 4,917,672 A * | 4/1990 | Terndrup | A61M 5/326 | 604/263 |
| 2008/0171986 A1* | 7/2008 | Baid | A61M 25/0618 | 604/164.08 |
| 2012/0123332 A1* | 5/2012 | Erskine | A61M 5/158 | 604/110 |
| 2015/0297867 A1* | 10/2015 | Howell | A61M 5/158 | 156/60 |

FOREIGN PATENT DOCUMENTS

CN 111643764 A * 9/2020 .......... A61M 5/3216

OTHER PUBLICATIONS

CN111643764A translation (Year: 2025).*

* cited by examiner

*Primary Examiner* — David N Brandt

(57) ABSTRACT

The present disclosure provides a safe puncture needle, and relates to the technical field of medical devices, which comprises a needle holder, a base and a needle tubing, wherein the needle tubing comprises a needle tubing body and a needle tubing tip having a bent structure, the base comprises a base body and a guide block, the base body is provided with a second inner space, the base body is provided with a first through-hole and a second through-hole communicating with the second inner space, the guide block is provided with a third through-hole, the needle tubing body passes through the first through-hole and the third through-hole and is slidably connected to the guide block, and the needle tubing tip retracts from the second through-hole.

11 Claims, 4 Drawing Sheets

SAFE PUNCTURE NEEDLE

CROSS-REFERENCE TO RELATED APPLICATION

This application claims priority from the Chinese patent application 202222394755.7 filed Sep. 7, 2022, the content of which are incorporated herein in the entirety by reference.

TECHNICAL FIELD

The disclosure relates to the technical field of medical devices, and specifically relates to a safe puncture needle.

BACKGROUND ART

After use of medical devices such as disposable infusion needles, it is often necessary for the medical care personnel to sealingly place the needle cover over the needle to prevent the sharp needle from directly exposing to prick the medical care personnel and the patient. However, in this operation mode, if the medical care personnel make mistakes in the process of setting the needle set, it is very easy to cause needle prick injury and even the risk of cross infection.

SUMMARY

A problem to be solved by the present disclosure is how to avoid needle pricking medical care personnel.

In order to solve the above-mentioned problems, the present disclosure provides a safe puncture needle comprising a needle holder, a base and a needle tubing, wherein the needle tubing comprises a needle tubing body and a needle tubing tip having a bent structure, the base comprises a base body and a guide block, the base body is provided with a second inner space, an upper end and a lower end of the base body are respectively provided with a first through-hole and a second through-hole communicating with the second inner space, the guide block is provided with a third through-hole and is connected to the base body in the second inner space, one end of the needle tubing body passes through the first through-hole and is connected to the needle holder, the other end is connected to the needle tubing tip and is used for passing through the third through-hole, and the needle tubing body is slidably connected to the guide block at the third through-hole, and the needle tubing tip is used for retracting from the second through-hole.

Alternatively, the base further comprises an elastic member and a shield, the elastic member is located in the second inner space and has one end connected to the base body and the other end connected to the shield for shielding the needle tubing tip when the needle tubing tip is retracted.

Alternatively, the shield is provided with a slide and the base body is provided with a first slide groove, and the slide is slidably connected to the base body at the first slide groove.

Alternatively, the base body includes an upper base and a lower base, the upper base and the lower base being sealingly connected to form the second inner space, the first through-hole being provided at the upper base, and the second through-hole being provided at the lower base.

Alternatively, one of the upper base and the lower base is provided with a positioning hole, and the other is provided with a positioning post inserted into the positioning hole.

Alternatively, the base further comprises a skin-friendly member provided on an outer surface of a lower end of the base body.

Alternatively, the safe puncture needle further comprises a rivet member, the rivet member comprising a flanging portion and a main body portion connected to each other, the rivet member being provided with a fourth through-hole passing through the flanging portion and the main body portion, the main body portion being slidably connected to the base body at the first through-hole, the needle tubing body passing through the fourth through-hole, the forward projection of the needle tubing tip on the end face of the flanging portion facing away from the main body portion is located at least partially outside the fourth through-hole, and the forward projection of the flanging portion on the upper end face of the base body is located at least partially outside the first through-hole.

Alternatively, one of the base body and the needle holder is provided with a guide insert and the other with a guide groove, and the guide insert is slidably connected to the guide groove.

Alternatively, the lower end of the base body is provided with a fifth through-hole communicating with the second inner space, and the fifth through-hole is located on a side of the shield facing away from the elastic member.

Alternatively, the third through-hole corresponds to the position of the second through-hole and that the needle tubing tip is adapted to be retracted into the third through-hole.

After using the safe puncture needle of the present disclosure, the medical care personnel can push the base or pull the needle holder so that the base moves relatively in a direction away from the needle holder, and then retract the needle tubing tip from the second through-hole to avoid direct exposure of the needle tubing tip after use, and solve the problems of the needle tubing tip pricking the medical care personnel and patients and causing cross infection, etc.; in addition, by providing a guide block in sliding connection with the needle tubing body, the relative movement between the base and the needle tubing is guided, so that the needle tubing is prevented from being deflected during the movement, and at the same time, since the needle tubing tip is of a bent structure, it is difficult to pass through the first through-hole to a certain extent, so that the needle tubing tip is prevented from being detached from the base due to excessive force applied by medical care personnel or the needle tubing being deflected.

DESCRIPTION OF REFERENCE NUMERALS

Figure 1:
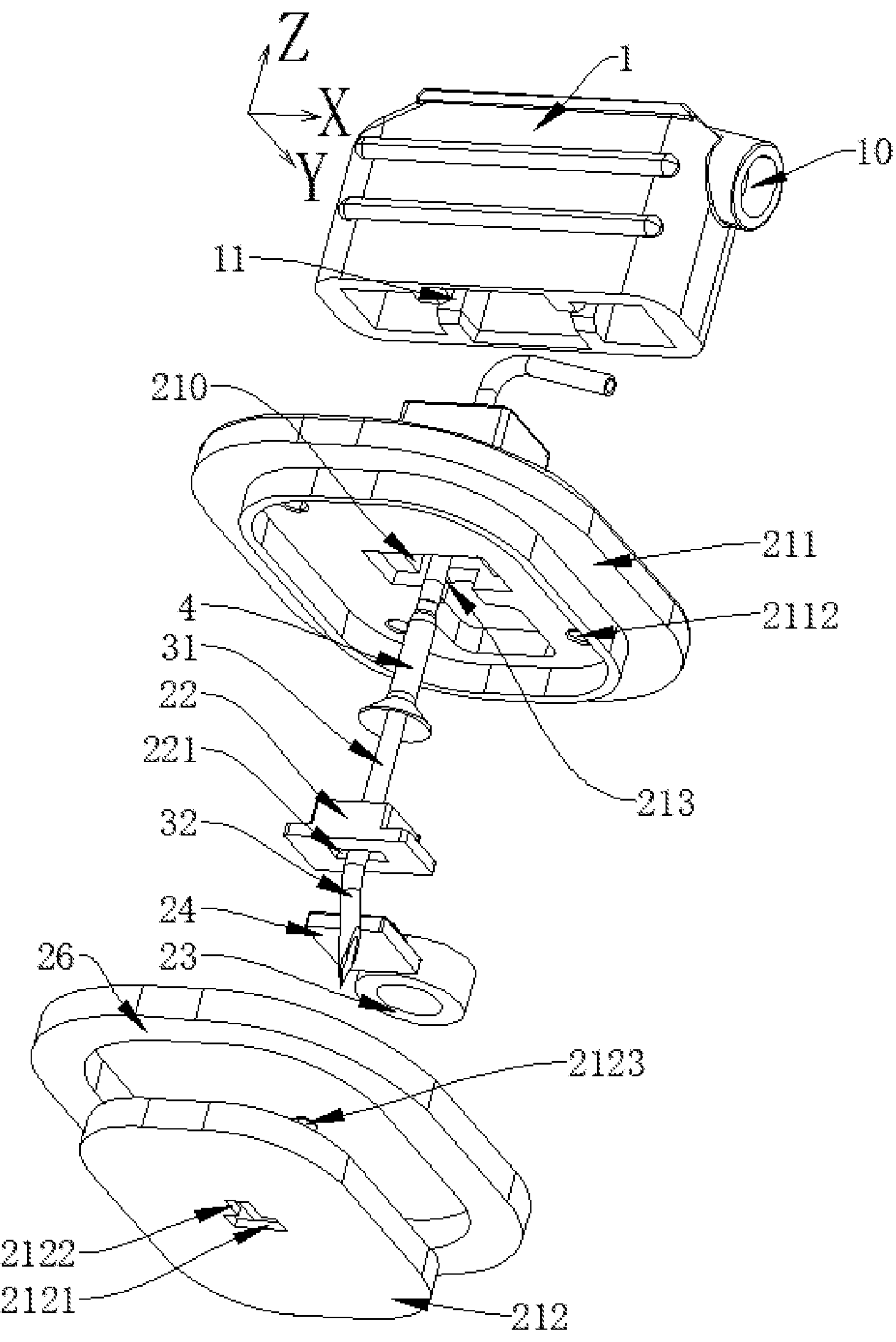
FIG. 1 is a three-dimensional structure explosion schematic diagram of a safe puncture needle according to an embodiment of the present disclosure.

1, needle holder; 10, first inner space; 11, guide slot; 2, base; 21, base body; 210, second inner space; 211, an upper base; 2111, first through-hole; 2112, positioning holes; 212, lower base; 2121, second through-hole; 2122, fifth through-hole; 2123, positioning post; 213, first chute; 214, second chute; 22, guide block; 221, third through-hole; 23, elastic member; 24, shield; 241, slide; 25, guide insert; 26, skin-friendly member; 3, needle tubing; 31, needle tubing body; 32, needle tubing tip; 4, rivet member; 41, flanging portion; 42, main body portion; 43, fourth through-hole.

DETAILED DESCRIPTION OF THE DISCLOSURE

In order that the above objects, features and advantages of the present disclosure can be more clearly understood, a detailed description of embodiments of the present disclosure will be given below with reference to the accompanying drawings.

It should be noted that in the coordinate system XYZ provided herein, the positive direction of X axis represents the right side, the reverse direction of X axis represents the left side, the positive direction of Y axis represents the rear side, the reverse direction of Y axis represents the front side, the positive direction of Z axis represents the upper side, and the reverse direction of Z axis represents the lower side. Meanwhile, it is noted that the terms "first", "second", and the like in the description and in the claims of the present disclosure and in the above-described drawings are used for distinguishing between similar objects and not necessarily for describing a particular sequential or chronological order. It is to be understood that the data so used are interchangeable under appropriate circumstances such that the embodiments of the present disclosure described herein are capable of operation in sequences other than those illustrated or otherwise described herein.

The present disclosure provides a safe puncture needle comprising a needle holder 1, a base 2 and a needle tubing 3, wherein the needle tubing 3 comprises a needle tubing body 31 and a needle tubing tip 2 having a bent structure, the base 2 comprises a base body 21 and a guide block 22, the base body 21 is provided with a second inner space 210, an upper end and a lower end of the base body 21 are respectively provided with a first through-hole 2111 and a second through-hole 2121 communicating with the second inner space 210, the guide block 22 is provided with a third through-hole 221 and is connected to the base body 21 in the second inner space 210, one end of the needle tubing body 31 passes through the first through-hole 2111 and is connected to the needle holder 1, the other end is connected to the needle tubing tip 32 and is used for passing through the third through-hole 221, and the needle tubing body 31 is slidably connected to the guide block 22 at the third through-hole 221, and the needle tubing tip 32 is used for retracting from the second through-hole 2121.

Figure 2:
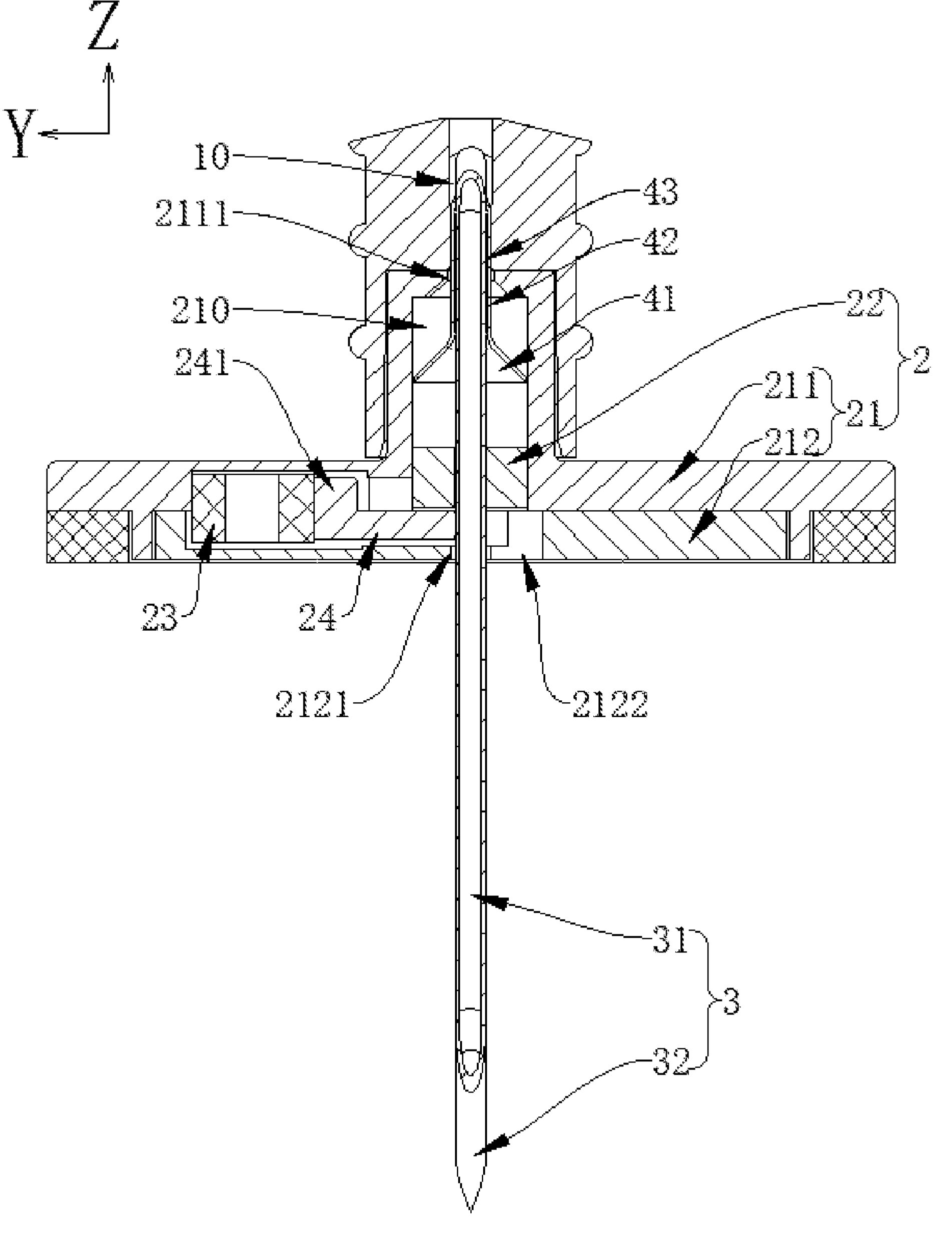
FIG. 2 is a schematic cross-sectional view of the safe puncture needle when the needle tubing tip according to an embodiment of the present disclosure protrudes.
Figure 3:
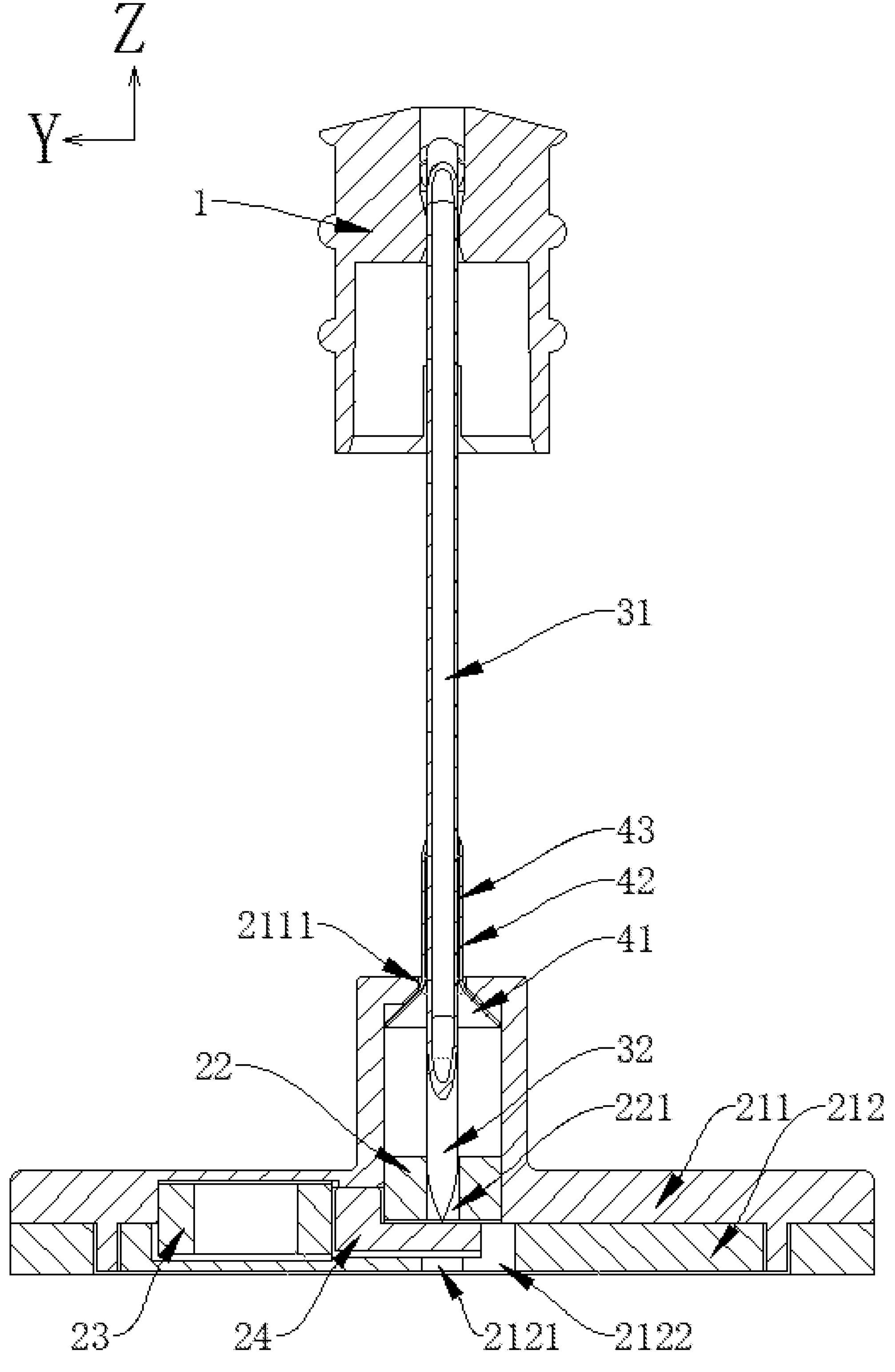
FIG. 3 is a schematic cross-sectional view of the safe puncture needle when the needle tubing tip according to an embodiment of the present disclosure is retracted.

Specifically, in conjunction with FIGS. 1-3, the upper end of the needle tubing 3 (i.e., one end in the positive direction along the Z axis in the figure) is located in the first inner space 10 of the needle holder 1, one end of the needle holder 1 in the positive direction along the X axis in the FIG. and one end in the opposite direction along the Z axis in the FIG. are respectively provided with a through-hole in communication with the first inner space 10 to facilitate the connection of the needle tubing 3 with other e.g. catheters and facilitate the downward extension of the needle tubing 3 through the needle holder 1, and the parameters (e.g. parameters such as the radius and angle of bending) of the needle tubing tip 32 of the bending structure can be specifically designed according to practical requirements. The base body 21 is equivalent to a housing structure having a cavity, and the cavity thereof is a second inner space 210; an upper end and a lower end of the base body 21 (i.e., two ends in the positive and negative directions along the Z axis in the figure) are respectively provided with a first through-hole 2111 and a second through-hole 2121, wherein the first through-hole 2111 can be a circular hole, a tapered hole or a hole structure of other shapes; the inner wall of the base body 21 facing the second inner space 210 is provided with a rectangular groove; the guide block 22 can be designed as a rectangular block structure so as to be placed in the rectangular groove; movement of the guide block 22 in the XY plane of the drawing is restricted, and part of the outer surface of the needle tubing body 31 is slidably coupled with the guide block 22 in the third through-hole 221.

It should be noted that since the needle tubing tip 32 is of a bent structure, it would have been readily conceivable to set the aperture of the first through-hole 2111 to be smaller than the outer diameter of the needle tubing tip 32 so as to avoid the needle tubing tip 32 escaping from the base body 21 from the first through-hole 2111, and set the aperture of the second through-hole 2121 to be greater than or equal to the outer diameter of the needle tubing tip 32 so as to facilitate the extension or retraction of the needle tubing tip 32 from the second through-hole 2121, and the specific size range thereof is not limited herein.

Illustratively, use of the safe puncture needle is described as follows: in conjunction with FIG. 2, the needle tubing tip 32 is in an extended state, and at this time, the needle tubing body 31 successively passes through the first through-hole 2111, the third through-hole 221 and the second through-hole 2121 from top to bottom, and the medical care personnel can hold the needle holder 1 so as to perform operations such as puncture and infusion on the patient; as shown in connection with FIG. 3, after use, the medical care personnel pushes the base 2 in the reverse direction of the Z-axis in the figure (i.e. away from the needle holder 1) or pulls the needle holder 1 in the forward direction of the Z-axis in the FIG. (i.e. away from the base 2) until the needle tubing tip 32 is retracted from the second through-hole 2121 (either into the second through-hole 2121 or into the second inner space 210).

It should be noted that in the present embodiment, the first through-hole 2111 may be eccentric with respect to the second through-hole 2121, i.e., the needle tubing 3 may adopt a non-linear structure, for example, the needle tubing body 31 also adopts a bent structure, which can also realize the retraction of the needle tubing tip 32, and the first through-hole 2111 and the second through-hole 2121 are not particularly limited.

After using the safe puncture needle of the present disclosure, the medical care personnel can push the base 2 or pull the needle holder 3 so that the base 2 moves relatively in a direction away from the needle holder 1, and then retract the needle tubing tip 32 from the second through-hole 2121 to avoid direct exposure of the needle tubing tip 32 after use, and solve the problems of the needle tubing tip 32 pricking the medical care personnel and patients and causing cross infection, etc.; in addition, by providing a guide block 22 in sliding connection with the needle tubing body 31, the relative movement between the base 2 and the needle tubing 3 is guided, so that the needle tubing 3 is prevented from being deflected during the movement, and at the same time, since the needle tubing tip 32 is of a bent structure, it is difficult to pass through the first through-hole 2111 to a certain extent, so that the needle tubing tip 32 is prevented from being detached from the base 2 due to excessive force applied by medical care personnel or the needle tubing 3 being deflected.

Alternatively, the base 2 further comprises an elastic member 23 and a shield 24, the elastic member 23 is located in the second inner space 210 and has one end connected to the base body 21 and the other end connected to the shield 24 for shielding the needle tubing tip 32 when the needle tubing tip 32 is retracted Specifically, as shown in FIG. 1 to FIG. 3, the elastic member 23 is a rubber ring (theoretically, an elastic structure such as a spring or the like may be used), and its rear end (i.e. one end in the positive direction of the Y axis in the figure) abuts against the inner wall surface of the base body 21 facing the second inner space 210, and its front end (i.e. one end in the opposite direction of the Y axis in the figure) abuts against the rear end of the shield 24. In conjunction with the schematic view of FIG. 2 when the needle tubing tip 32 is extended, the front end of the shield 24 abuts and is slidably connected to the outer surface of the needle tubing 3, and in conjunction with the schematic view of FIG. 3 when the needle tubing tip 32 is retracted, when the outer surface of the needle tubing 3 no longer abuts with the front end of the shield 24, the shield 24 is moved in the opposite direction of the Y-axis in the figure by the elastic force of the elastic member 23 to move below the needle tubing tip 32 and shield the needle tubing tip 32.

Thus, the elastic potential energy of the elastic member 23 is converted into kinetic energy, and the shield 24 can be driven to move in a direction away from the elastic member 23 after the needle tubing tip 32 is retracted, thereby shielding the needle tubing tip 32 and preventing the sharp part of the needle tubing 3 from being directly exposed, thereby preventing the medical care personnel and the patient from being pricked or even cross-infected.

Alternatively, the shield 24 is provided with a slide 241, the base body 21 is provided with a first sliding groove 213, and the slide 241 and the base body 21 are slidably connected at the first sliding groove 213.

Specifically, as shown in connection with FIGS. 1-3, the slide 241 is integrally connected with the shield 24, and the first slide groove 213 is provided along the Y-axis in the drawing, and the shield 24 is moved along the first slide groove 213 by the slide 241 when the needle tubing tip 32 is retracted and the elastic member 23 drives the shield 24 in the reverse direction of the Y-axis.

For example, when the base body 21 is formed by connecting the upper base 211 and the lower base 212 to each other (the specific structure thereof will be described later), in conjunction with FIGS. 1-3 and 5, the lower base 212 is provided with a second sliding groove 214, the shield 24 itself is also equivalent to a slide, and is slidably connected to the lower base 212 in the second sliding groove 214, the upper base 211 is provided with a first sliding groove 213, and the slide 241 connected to the shield 24 is slidably connected to the upper base 211 in the first sliding groove 213. The upper base 211 and the lower base 212 are respectively provided with a square groove, and when the upper base 211 is connected to the lower base 212, the space formed by the two square grooves can accommodate the elastic member 23 (a rubber ring is taken as an example in the figure), i.e., the second inner space 210 in the present embodiment is composed of the above-mentioned two square grooves, the first sliding groove 213, the second sliding groove 214 and other spatial structures.

In this manner, deflection of the shield 24 when moving in a direction away from elastomeric member 23 can be avoided, resulting in incomplete shielding of the needle tubing tip 32 or jamming of shield 24.

Alternatively, the base body 21 includes an upper base 211 and a lower base 212, the upper base 211 and the lower base 212 are hermetically connected to form the second inner space 210, the first through-hole 2111 is provided at the upper base 211, and the second through-hole 2121 is provided at the lower base 212.

Specifically, as shown in conjunction with FIGS. 1-3 and 5, the upper base 211 is provided with a side wall structure in an annular arrangement, and the side wall structure can be sheathed on the lower base 212 to achieve a sealing connection (a component having a sealing function such as a sealing ring can also be added).

Thus, the sealed connection between the upper base 211 and the lower base 212 limits the components in the second inner space 210 and prevents dust and the like from entering the interior of the safe puncture needle.

Alternatively, one of the upper base 211 and the lower base 212 is provided with a positioning hole 2112, and the other is provided with a positioning post 2123, and the positioning post 2123 is inserted into the positioning hole 2112.

Figure 5:
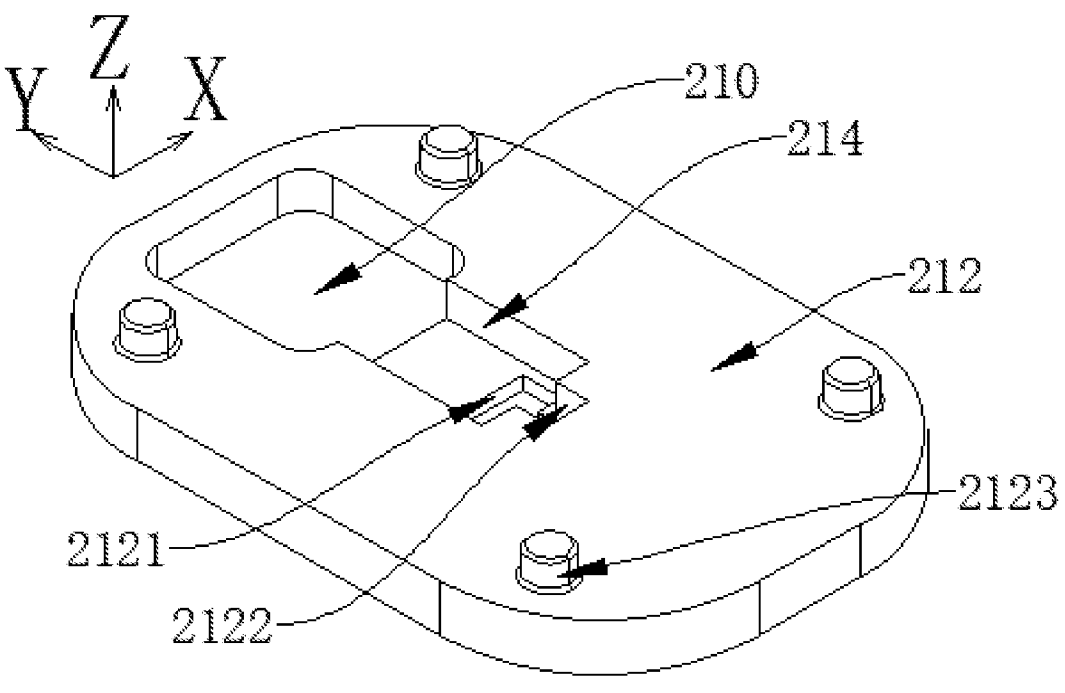
FIG. 5 is a schematic diagram of the three-dimensional structure of the lower base according to an embodiment of the present disclosure.

Specifically, as shown in conjunction with FIGS. 1 and 5, since the lower base 212 has a structure similar to a rectangular block, four positioning posts 2123 facing in the positive direction of the Z axis in the figure are provided, which are provided at positions near four right-angled ends of the lower base 212, and correspondingly, the upper base 211 is provided with four positioning holes 2112 having the same shape facing in the opposite direction of the Z axis in the figure.

In this manner, the positioning post 2123 and the positioning hole 2112 can easily and quickly align the upper base 211 with the lower base 212 and achieve a sealing connection.

Alternatively, the base 2 further comprises a skin-friendly member 26 provided on the outer surface of the lower end of the base body 21.

Specifically, in conjunction with FIGS. 1-3, the skin-friendly member 26 is provided on the outer side of the side wall structure provided in a circular arrangement on the upper base 211, i.e., the skin-friendly member 26 is also provided in a circular arrangement, wherein the skin-friendly member 26 can be made of a material such as medical sponge, and one end thereof is adhered to the upper base 211, and the other end thereof is provided in a direction opposite to the Z axis in the figure.

In this manner, the skin-friendly member 26 may directly contact the patient's skin to enhance the patient's experience when performing a puncture infusion or the like on the patient.

Alternatively, the safe puncture needle further comprises a rivet member 4 comprising a flanging portion 41 and a main body portion 42 connected to each other, the rivet member 4 being provided with a fourth through-hole 43 passing through the flanging portion 41 and the main body portion 42, the main body portion 42 being slidably connected to the base body 21 at the first through-hole 2111, the needle tubing body 31 passing through the fourth through-hole 43, the forward projection of the needle tubing tip 32 on the end face of the flanging portion 41 facing away from the main body portion 42 is located at least partially outside the fourth through-hole 43, and the forward projection of the flanging portion 41 on the upper end face of the base body 21 is located at least partially outside the first through-hole 2111.

Specifically, in conjunction with FIGS. 1-3, the main body portion 42 of the rivet member 4 is of a sleeve-like structure, the central hole (i.e., the fourth through-hole 43) thereof is sleeved on the needle tubing body 31, the flanging portion 41 can be of a conical cylindrical structure (or a circular ring-shaped structure parallel to the XY plane in the figure), a countersink is provided at the first through-hole 2111 of the upper base 211 towards the second inner space 210 (when the flanging portion 41 is of a conical cylindrical structure, the countersink is also a conical countersink, i.e., the shape of the countersink can be designed according to the shape of the flanging portion 41), and since the needle tubing tip 32 is of a bent structure, the forward projection of the needle tubing tip 32 on the plane of the end face of the flanging portion 41 in the direction opposite to the Z axis in the drawing is partially outside the fourth through-hole 43, so that the needle tubing tip 32 cannot pass through the fourth through-hole 43 when the needle tubing 3 moves linearly along the Z axis in the drawing, and it can be understood that the forward projection of the flanging portion 41 on the plane of the end face of the upper end of the base body 21 is also partially outside the first through-hole 2111, so that the flanging portion 41 cannot pass through the first through-hole 2111 when the rivet member 4 moves linearly along the Z axis in the drawing.

In this manner, upon retraction of the needle tubing tip 32, the needle tubing tip 32 abuts the fourth through-hole 43 and moves the flanged portion 41 toward the first through-hole 2111 until the flanged portion 41 abuts the first through-hole 2111, thereby preventing the needle tubing tip 32 from disengaging the base body 21.

Alternatively, one of the base body 21 and the needle holder 1 is provided with a guide insert 25, and the other is provided with a guide slot 11, to which the guide insert 25 is slidably connected.

Figure 4:
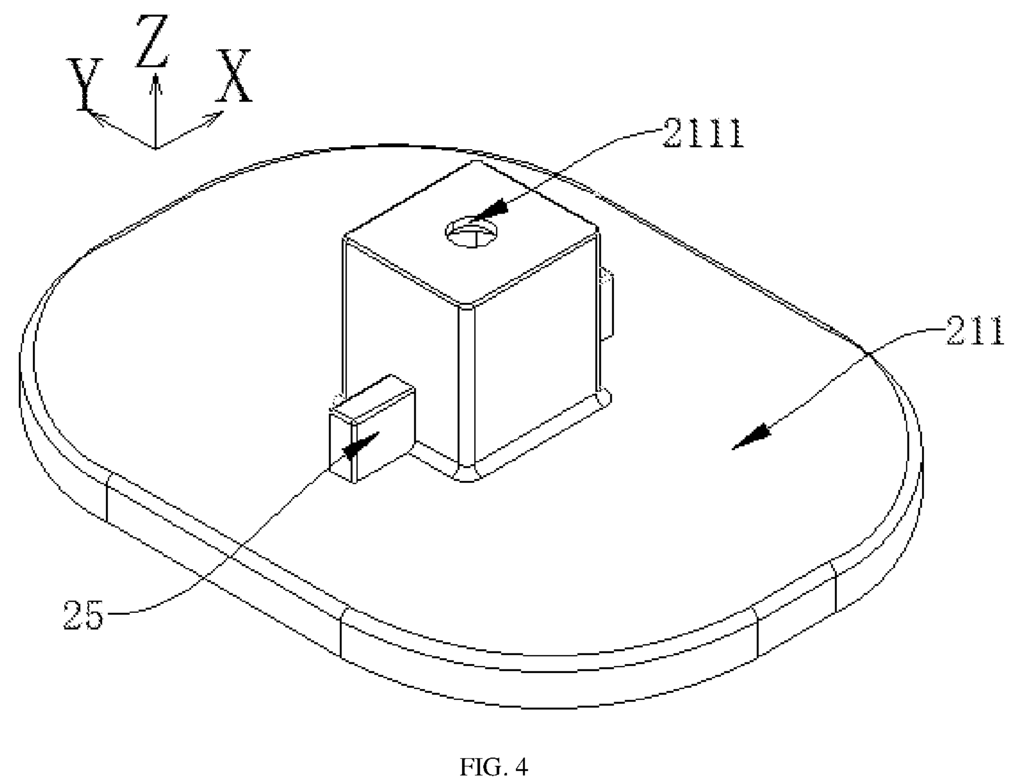
FIG. 4 is a schematic diagram of the three-dimensional structure of the upper base according to an embodiment of the present disclosure.

Specifically, as shown in conjunction with FIGS. 1 and 4, in the base body 21, the ZY plane in the FIG. is a symmetrical plane, two guide inserts 25 are symmetrically provided on the base body 21; correspondingly, the end face of the needle holder 1 facing the base body 21 is provided with a guide slot 11; when the needle tubing tip 32 is retracted, the guide inserts 25 move downwards along with the base body 21 and are guided by the guide slot 11 until the guide inserts 25 are separated from the guide slot 11, and then the base body 21 continues to move until the needle tubing tip 32 is completely retracted.

Thus, the guide insert 25 cooperates with the guide slot 11 to perform a guide function for the base body 21.

Alternatively, the lower end of the base body 21 is provided with a fifth through-hole 2122 communicating with the second inner space 210, the fifth through-hole 2122 being located at a side of the shield 24 facing away from the elastic member 23.

In particular, as shown in connection with FIGS. 1 to 3, the fifth through-hole 2122 and the second through-hole 2121 form a T-shaped through-hole structure, the fifth through-hole 2122 being located at the front side of the second through-hole 2121, and as shown in connection with FIGS. 2 and 3, the fifth through-hole 2122 is still located at a side of the shield 24 facing away from the elastic member 23 after the needle tubing tip 32 is retracted.

Note that the fifth through-hole 2122 may also be provided as a separate through-hole structure at the lower end of the base body 21 on a side of the shield 24 facing away from the elastic member 23, and its specific shape may be designed as required, without limitation.

In this way, when it is required to assemble the needle tubing 3, the needle tubing 3 can be inserted from the fifth through-hole 2122 to a side of the shield 24 facing away from the elastic member 23, and the elastic member 23 is compressed by pulling the shield 24 towards the elastic member 23, thereby aligning the needle tubing 3 with the guide block 22 to perform an assembly insertion operation, which is convenient and quick.

Alternatively, the third through-hole 221 corresponds in position to the second through-hole 2121, and the needle tubing tip 32 is adapted to retract into the third through-hole 221.

Specifically, as shown in conjunction with FIGS. 1-3, the third through-hole 221 and the second through-hole 2121 are both rectangular holes, the positions of which correspond to each other (it can be understood that the central positions of the two project on the same XY horizontal plane, and the projected positions thereof coincide, or have only a slight deviation), the width of the rectangular hole (i.e., the dimension in the direction of the Y axis in the figure) should be equal to the outer diameter of the needle tubing tip 32 or have a certain interference fit so as to achieve the guiding function, and the forward projection of the needle tubing tip 32 on the lower end face of the base body 21 should be located in the second through-hole 2121, and the forward projection of the needle tubing tip 32 on the lower end face of the guide block 22 should be located in the third through-hole 221 so that the needle tubing tip 32 can pass smoothly.

In this way, the needle tubing tip 32 can be retracted into the third bore 221, facilitating a reduction in the overall size of the safe puncture needle (e.g. the lower base 212 may be appropriately reduced in thickness without causing the needle tubing tip 32 to protrude from the lower base 212).

Although the present disclosure has been described above, the endoscope of protection of the present disclosure is not limited thereto. Various changes and modifications can be made by a person skilled in the art without departing from the spirit and scope of the disclosure, which will fall within the scope of the present disclosure.

The invention claimed is:

1. A safe puncture needle, comprising a needle holder (1), a base (2) and a needle tubing (3), wherein the needle tubing (3) comprises a needle tubing body (31) and a needle tubing tip (32) having a bent structure, the base (2) comprises a base body (21) and a guide block (22), the base body (21) is provided with a second inner space (210), an upper end and a lower end of the base body (21) are respectively provided with a first through-hole (2111) and a second through-hole (2121) communicating with the second inner space (210), the guide block (22) is provided with a third through-hole (221) and is connected to the base body (21) in the second inner space (210), a first end of the needle tubing body (31) penetrates the first through-hole (2111) and is connected to the needle holder (1), a second end opposite to the first end of the needle tubing body (31) is connected to the needle tubing tip (32) and penetrates the third through-hole (221), and the needle tubing body (31) is slidably connected to the guide block (22) at the third through-hole (221), and the needle tubing tip (32) is configured to retract through the second through-hole (2121); wherein the safe puncture needle further comprises a rivet member (4) comprising a flanging portion (41) and a main body portion (42) connected to each other, the rivet member (4) comprises a fourth through-hole (43) penetrating the flanging portion (41) and the main body portion (42), the main body portion (42) is slidably connected to the base body (21) along the first through-hole (2111), the needle tubing body (31) penetrates the fourth through-hole (43); the flanging portion (41) is a conical cylindrical structure, a dimension of an upper end of the flanging portion (41) in contact with the main body portion (42) in a plane perpendicular to the main body portion (42) is smaller than a dimension of a lower end of the flanging portion (41) in the plane perpendicular to the main body portion (42).

2. The safe puncture needle according to claim 1, wherein the base (2) further comprises an elastic member (23) and a shield (24), the elastic member (23) is located in the second inner space (210) and has one end connected to the base body (21) and an other end of the elastic member (23) connected to the shield (24) for shielding the needle tubing tip (32) when the needle tubing tip (32) is retracted.

3. The safe puncture needle according to claim 2, wherein the shield (24) is provided with a slide (241) and the base body (21) is provided with a first slide groove (213), and the slide (241) is slidably connected to the base body (21) at the first slide groove (213).

4. The safe puncture needle according to claim 1, wherein the base body (21) comprises an upper base (211) and a lower base (212), the upper base (211) is sealingly connected to the lower base (212) to form the second inner space (210), the first through-hole (2111) is provided at the upper base (211), and the second through-hole (2121) is provided at the lower base (212).

5. The safe puncture needle according to claim 4, wherein one of the upper base (211) and the lower base (212) is provided with a positioning hole (2112), and an other one of the upper base (211) and the lower base (212) is provided with a positioning post (2123), and the positioning post (2123) is inserted into the positioning hole (2112).

6. The safe puncture needle according to claim 1, wherein the base (2) further comprises a medical sponge structure surrounding the base body (21).

7. The safe puncture needle according to claim 1, wherein a projection of the needle tubing tip (32) on a surface of the flanging portion (41) facing away from the main body portion (42) is located at least partially outside the fourth through-hole (43), and a projection of the flanging portion (41) on an upper surface of the base body (21) is located at least partially outside the first through-hole (2111).

8. The safe puncture needle according to claim 1, wherein one of the base body (21) and the needle holder (1) is provided with a guide insert (25) and an other one of the base body (21) and the needle holder (1) is provided with a guide groove (11), and the guide insert (25) is slidably connected to the guide groove (11).

9. The safe puncture needle according to claim 2, wherein the lower end of the base body (21) is provided with a fifth through-hole (2122) communicating with the second inner space (210), and the fifth through-hole (2122) is located on a side of the shield (24) facing away from the elastic member (23).

10. The safe puncture needle according to claim 1, wherein the third through-hole (221) corresponds to a position of the second through-hole (2121) and that the needle tubing tip (32) is adapted to be retracted into the third through-hole (221).

11. The safe puncture needle according to claim 1, wherein the first through-hole (2111) is a conical countersink, a dimension of an upper end of the first through-hole (2111) in the plane perpendicular to the main body portion (42) is smaller than a dimension of a lower end of the first through-hole (2111) in the plane perpendicular to the main body portion (42).

* * * * *